(12) United States Patent
Johnson et al.

(10) Patent No.: US 9,700,249 B2
(45) Date of Patent: Jul. 11, 2017

(54) NON-INVASIVE OPTICAL SENSOR

(75) Inventors: Timothy L. Johnson, Plymouth, MN (US); Franz Ulrich, Minneapolis, MN (US); Philip O. Isaacson, Chanhassen, MN (US)

(73) Assignee: Nonin Medical, Inc., Plymouth, MN (US)

(*) Notice: Subject to any disclaimer, the term of this patent is extended or adjusted under 35 U.S.C. 154(b) by 1189 days.

(21) Appl. No.: 12/423,985

(22) Filed: Apr. 15, 2009

(65) Prior Publication Data

US 2009/0259114 A1    Oct. 15, 2009

Related U.S. Application Data

(60) Provisional application No. 61/045,180, filed on Apr. 15, 2008.

(51) Int. Cl.
*A61B 5/1455* (2006.01)
*A61B 5/00* (2006.01)

(52) U.S. Cl.
CPC ...... *A61B 5/14553* (2013.01); *A61B 5/14552* (2013.01); *A61B 5/6825* (2013.01); *A61B 5/6833* (2013.01); *A61B 5/6843* (2013.01)

(58) Field of Classification Search
CPC .... A61B 5/6843; A61B 5/6833; A61B 5/6825
USPC .................................. 600/310, 323
See application file for complete search history.

(56) References Cited

U.S. PATENT DOCUMENTS

| | | | | |
|---|---|---|---|---|
| 5,217,013 A | * | 6/1993 | Lewis | A61B 5/0091 356/41 |
| 5,429,129 A | * | 7/1995 | Lovejoy | A61B 5/6833 600/310 |
| 5,465,714 A | * | 11/1995 | Scheuing | A61B 5/14552 600/323 |

(Continued)

FOREIGN PATENT DOCUMENTS

| | | |
|---|---|---|
| JP | 09206283 A | 8/1997 |
| JP | 2001087250 A | 4/2001 |

(Continued)

OTHER PUBLICATIONS

"International Application Serial No. PCT/US2009/002345, International Search Report mailed Aug. 19, 2009", 7 pgs.

(Continued)

*Primary Examiner* — Michael C Stout
(74) *Attorney, Agent, or Firm* — Schwegman Lundberg & Woessner, P.A.

(57) ABSTRACT

An apparatus includes a sensor body, a circuit board, a cable, at least one light emitting device, and at least one photodetector. The circuit board is enclosed within the sensor body and includes at least one conductive trace and at least one aperture. The cable is coupled to the at least one conductive trace. The cable includes a shield conductor and a signal conductor. The at least one light emitting device is coupled to the circuit board and is configured to emit light into a tissue. The at least one photodetector includes a planar active area coupled to the circuit board and is configured to provide an output signal based on light detected by the active area. The planar active area is aligned with the aperture. The output signal is coupled to the cable.

35 Claims, 7 Drawing Sheets

(56) References Cited

U.S. PATENT DOCUMENTS

| | | | |
|---|---|---|---|
| 5,520,177 A * | 5/1996 | Ogawa | A61B 5/14552 600/323 |
| 5,584,296 A * | 12/1996 | Cui | A61B 5/14552 356/41 |
| 5,697,367 A | 12/1997 | Lewis et al. | |
| 5,752,914 A * | 5/1998 | Delonzor | A61B 5/14552 442/131 |
| 5,795,292 A | 8/1998 | Lewis et al. | |
| 5,817,008 A * | 10/1998 | Rafert | A61B 5/14552 600/323 |
| 5,891,026 A | 4/1999 | Wang et al. | |
| 5,893,364 A | 4/1999 | Haar et al. | |
| 6,086,247 A * | 7/2000 | von Hollen | A61B 5/015 374/137 |
| 6,184,521 B1 * | 2/2001 | Coffin, IV | A61B 5/14552 250/216 |
| 7,392,074 B2 | 6/2008 | Isaacson et al. | |
| 7,486,977 B2 * | 2/2009 | Sweitzer | A61B 5/14552 250/505.1 |
| 7,791,155 B2 * | 9/2010 | Diab | 257/435 |
| 7,865,223 B1 | 1/2011 | Bernreuter | |
| 8,116,838 B2 * | 2/2012 | Gaspard | A61B 5/0075 600/322 |
| 8,170,636 B2 * | 5/2012 | Cinbis | A61B 5/0031 600/310 |
| 2001/0034479 A1 * | 10/2001 | Ring | A61B 5/14556 600/322 |
| 2003/0225323 A1 * | 12/2003 | Kiani | A61B 5/0478 600/323 |
| 2006/0189860 A1 * | 8/2006 | Hacker | A61B 5/14552 600/323 |
| 2007/0100218 A1 * | 5/2007 | Sweitzer | A61B 5/0002 600/323 |
| 2007/0100219 A1 | 5/2007 | Sweitzer et al. | |
| 2007/0142715 A1 | 6/2007 | Banet et al. | |
| 2007/0163894 A1 * | 7/2007 | Wang | A61B 5/1495 205/792 |
| 2007/0208233 A1 * | 9/2007 | Kovacs | 205/792 |
| 2007/0276262 A1 * | 11/2007 | Banet | A61B 5/0205 600/300 |
| 2008/0015424 A1 | 1/2008 | Bernreuter | |
| 2008/0170379 A1 * | 7/2008 | Basoor | A61B 5/02255 600/485 |
| 2008/0197301 A1 * | 8/2008 | Diab | H05K 9/0058 361/818 |
| 2009/0234206 A1 * | 9/2009 | Gaspard | A61B 5/0002 600/323 |
| 2009/0301891 A1 * | 12/2009 | Locktman | A61B 5/0059 600/301 |
| 2009/0312613 A1 * | 12/2009 | Henderson | A61B 5/0075 600/322 |
| 2009/0323267 A1 * | 12/2009 | Besko | C25D 7/0614 205/125 |
| 2010/0006327 A1 * | 1/2010 | Yu | A61B 5/14552 361/679.4 |
| 2010/0049018 A1 * | 2/2010 | Duffy | H05K 1/0284 174/258 |
| 2010/0301215 A1 * | 12/2010 | Gonopolskiy | A61B 5/1455 600/323 |
| 2010/0324384 A1 * | 12/2010 | Moon | A61B 5/0245 600/323 |
| 2011/0054285 A1 * | 3/2011 | Searle | A61M 5/14244 600/365 |

FOREIGN PATENT DOCUMENTS

| | | |
|---|---|---|
| JP | 2004113814 A | 4/2004 |
| WO | WO-9412096 A1 | 6/1994 |
| WO | WO-2009128914 A1 | 10/2009 |

OTHER PUBLICATIONS

"International Application Serial No. PCT/US2009/002345, Written Opinion mailed Aug. 19, 2009", 7 pgs.

Haahr, R G, et al., "A Novel Photodiode for Reflectance Pulse Oximetry in low-power applications", Engineering in Medicine and Biology Society, 2007. EMBS 2007. 29th Annual International Conference of the IEEE IEEE, Piscataway, NJ, USA,, XP031336677 ISBN: 978-1-4244-0787-3, (Aug. 22, 2007), 2350-2353.

"EP Application Serial No. 09733542.6 Amended Claims Response filed Mar. 31, 2011", 13 pgs.

European Application Serial No. 09733542.6, Office Action mailed Feb. 17, 2011, 2 pgs.

International Application Serial No. PCT/US2009/002345, International Preliminary Report on Patentability mailed Oct. 28, 2010, (Oct. 28, 2010).

Japanese Application Serial No. 2011-505020, Examiners Decision of Rejection mailed Sep. 30, 2014, 4 pgs.

Japanese Application Serial No. 2011-505020, Office Action mailed Nov. 19, 2013, (w/ English Translation), 6 pgs.

Japanese Application Serial No. 2011-505020, Response filed May 15, 2014 to Office Action mailed Nov. 19, 2013, 16 pgs.

Canadian Application Serial No. 2,724,017, Office Action mailed Nov. 9, 2015, 4 pgs.

"Canadian Application Serial No. 2,724,017, Response filed May 9, 2016 to Office Action mailed Nov. 9, 2015", 15 pgs.

* cited by examiner

NON-INVASIVE OPTICAL SENSOR

CLAIM OF PRIORITY

This patent application claims the benefit of priority, under 35 U.S.C. Section 119(e), to Johnson et al., U.S. Provisional Patent Application Ser. No. 61/045,180, entitled "Non-Invasive Optical Sensor" filed on Apr. 15, 2008, which is incorporated herein by reference in its entirety.

TECHNICAL FIELD

The present disclosure is directed to in vivo optical examination and monitoring of selected blood metabolites or constituents in human and/or other living subjects. More specifically, the present disclosure is directed to such examination and monitoring by transmitting selected wavelengths of light into a given area of the patient, receiving the resulting light as it leaves the patient, and analyzing the received light to determine the desired data based on light absorption.

BRIEF SUMMARY OF THE INVENTION

The present subject matter provides improvements in optical sensor assemblies, particularly adapted for in vivo use as the patient interface in a patient-monitoring apparatus such as a cerebral or tissue oximeter. The present subject matter relates generally to in vivo optical examination and monitoring of selected blood metabolites or constituents in human and/or other living subjects by transmitting selected wavelengths of light into a given area of the patient, receiving the resulting light as it exits the patient, and analyzing the received light to determine the desired constituent data from which information such as blood oxygen saturation may be determined.

One application and field of use of the present subject matter is the non-invasive determination of tissue oxygenation. A further extension of the technology is related to non-invasive cerebral oximeter, by which blood oxygen saturation in the brain may be non-invasively determined through the use of an optical sensor having light emitters and detectors that is applied to the forehead of the patient.

An example of the present subject matter provides an apparatus for in vivo monitoring of blood metabolites such as hemoglobin oxygen concentration in any of a plurality of different regions of a patient through application of a novel optical sensor assembly. The optical sensor assembly is coupled to a control and processing device, such as a monitor, that operates the sensor assembly to illuminate a particular region within the patient associated with the sensor assembly, detect and receive the light energy resulting from the illumination, convey signals corresponding to the light energy so received, analyze the conveyed signals to determine preselected blood metabolite data, and display the data so obtained.

An apparatus in accordance with one embodiment of the present subject matter provides an optical probe having a flexible support or component-carrier and being adapted for comfortably conforming to the shape of the patient's cerebrum or other such anatomical area.

The foregoing has outlined rather broadly the features and technical advantages of the present subject matter in order that the detailed description that follows may be better understood. Additional features and advantages will be described hereinafter which form the subject of the claims of the invention. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the present subject matter as set forth in the appended claims. The novel features which are believed to be characteristic of the present subject matter, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present subject matter.

BRIEF DESCRIPTION OF THE DRAWINGS

For a more complete understanding, reference is now made to the following descriptions taken in conjunction with the accompanying drawing, in which.

DETAILED DESCRIPTION OF THE INVENTION

A cerebral sensor assembly will be used by way of example in portions of the following description. However, it should be understood that other embodiments of the present subject matter could as well be applied to other types of physiological sensors, such as, for example, other types of tissue oximetry sensors for use on other locations on human and other living patients.

Figure 1A:
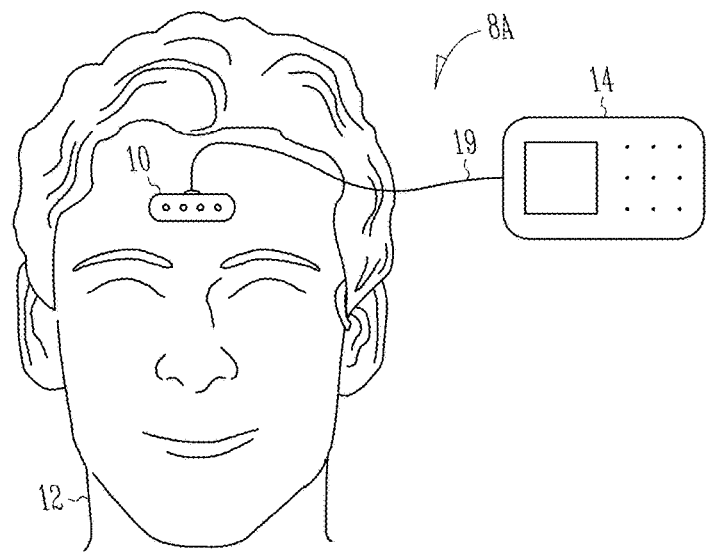
FIG. 1A is a perspective illustration of application of a sensor assembly in accordance with the present subject matter.

FIG. 1A is a pictorial showing of a setting in which the sensor assembly, in accordance with the subject matter, can be used, as part of an operative system for monitoring or examining blood oxygen saturation of patients. For purposes of the present disclosure, FIG. 1A shows a system 8A having a sensor assembly 10 on a human patient 12 who is being monitored by an oximetry monitor 14. Sensor assembly 10 is applied to the forehead of the patient 12 to optically access an internal tissue volume or regional field within the cerebrum, directly adjacent the point where sensor 10 is located, but inside of the scalp, skull, and adjacent dura, i.e., within the brain tissue itself. Sensor 10 is flexible and conforms to the forehead surface of patient 12.

The sensor assembly 10 is coupled to the oximetry monitor 14 through a cable 19 which includes individual conductors for energizing light emitters and operating the related light detectors contained in sensor assembly 10. The oximetry monitor 14, in this example, is a monitor on which visual displays may be perceived. A variety of different control and processing unit could also be implemented in a different system utilizing the sensor assembly of the present subject matter to provide oximetry or other physiological information. Monitor 14 can, in one example include memory for storage of data. In one example, monitor 14 does not include a visual display. The data stored in monitor 14 can be forwarded to another device or processor for subsequent storage or processing. The data can be communicated by a wired link or by a wireless link.

Figure 1B:
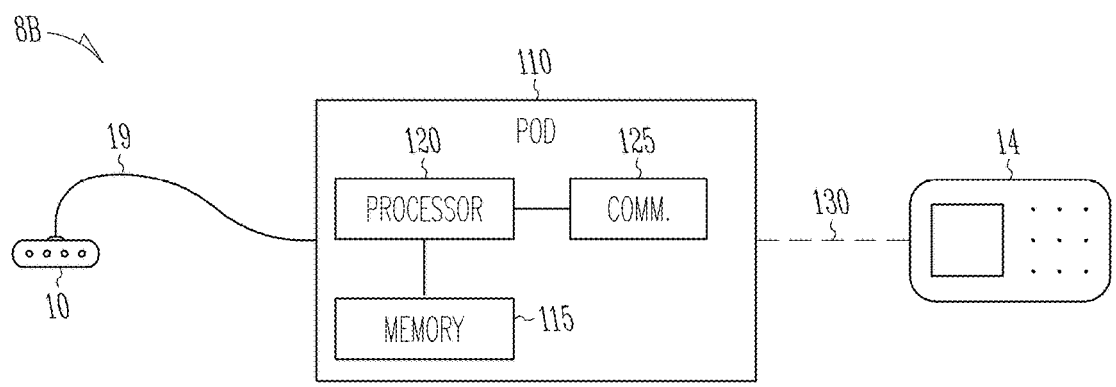
FIG. 1B is a block diagram of a sensor assembly in accordance with the present subject matter.

FIG. 1B illustrates system 8B having intermediary pod 110. Pod 110 is coupled to sensor assembly 10 by cable 19, as described elsewhere in this document. In one example, cable 19 carries a low level signal. Pod 110, in the example illustrated, includes processor 120, memory 115, and communication module 125, however, other examples can include more or less modules. Other modules also contemplated for pod 110 include an analog-to-digital converter (ADC), a digital-to-analog converter (DAC), a filter, an amplifier, and a power supply among others, some of which can be in the form of a discrete component or be implemented by means of processor 120. A power supply can include a battery. Processor 120, in the example illustrated includes programming (stored on memory 115) for executing an algorithm to evaluate or process data received from sensor assembly 10. Memory 115, in one example, includes storage for programming or instructions (for use by processor 120) and data corresponding to sensor assembly 10. In one example, pod 110 is configured as a component of monitor 14.

Communication module 125, in one example, includes a wired or wireless telemetry module for communicating with monitor 14 using communication link 130. For example, communication module 125 can include a Bluetooth wireless module in which case communication link 130 includes a radio frequency communication channel. Communication module 125, and communication link 130 can be bidirectional or unidirectional. In one example, communication module 125 includes an interface to allow exchange of a high level signal using a wired communication channel.

Generally speaking, the sensor assembly 10 includes an elongated member with rounded corners, from which cable 19 extends outwardly. The particular embodiment of the sensor assembly 10 shown in FIG. 2 comprises a laminar "sandwich" construction and includes a cover layer 30 having, for example, a soft, flexible sheet of foam material or the like and a frontal layer 32. Frontal layer 32 may be a two-side adhesive layer or may be a combination of two-sided adhesive with a light-blocking layer. Cover layer 30 may include a black PVC or polyethylene foam layer. An electrical circuit board 34 is disposed between layers 30, 32. The two layers 30, 32 are secured to circuit board 34, for example, via adhesive.

Electro-optical devices including photodetectors 40 and light emitting devices 42 are connected to circuit board 34. The photodetectors 40 and light emitting devices 42 are disposed in registration with appropriate apertures 50 extending through the circuit board 34 and frontal layer 32 and through which such optical components may access the patient 12 (by emitting light which transmisses through the scalp, skull and brain tissue of region, and then detecting resultant light after it leaves such region and passes back out of the patient through the skull and scalp, etc.).

The illustrated embodiment of sensor assembly 10 includes a pair of light emitting devices 42 and a pair of photodetectors 40. The sensor assembly 10 and monitor 14 may include subject matter disclosed in U.S. patent application Ser. No. 11/078,399, entitled In Vivo Blood Spectrometry, to P. Bernreuter, said application being incorporated by reference herein for all purposes.

In the illustrated embodiment, the electrical circuit board 34 is approximately the same size as the outer dimensions of the cover layer 30 and frontal layer 32, which provide the outwardly visible shape of sensor assembly 10. In alternative embodiments, the board 34 may sized differently than the cover or frontal layers 30, 32.

Figure 3:
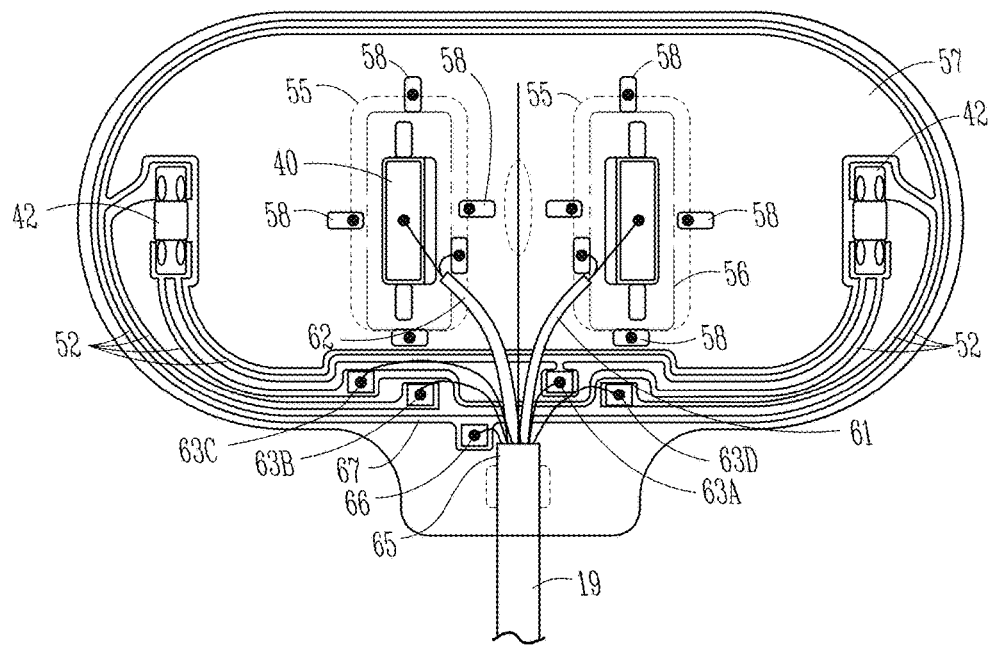
FIG. 3 is a top plan view of the sensor assembly of FIG. 2.

Referring to FIG. 3, circuit board 34 can include a printed circuit board having a support substrate and printed conductor traces 52 secured to one side. The photodetectors 40, as well as the light emitting devices 42, are electrically connected to the respective conductor traces 52. In one embodiment, the circuit board 34 may be of a flexible type, sometimes referred to as a flex circuit.

Separate copper shield elements 55 are positioned above light detecting devices 40. Insulators 56, such as an adhesive tape, electrically isolate shield elements 55 from the photodetectors 40. Circuit board 34 also defines a shield conductor 57 on the same plane as conductive traces 52. In the illustrated embodiment, shield conductor 57 extends generally across the circuit board 34. Apertures 50 extend through shield conductor 57. Foil shield elements 55, which may include a copper tape, are electrically connected to shield conductor 57 at multiple locations 58. These electrical connections between shield elements 55 and shield conductor 57 may be via techniques including, but not limited to, soldering, conductive epoxies, etc.

Figure 4:
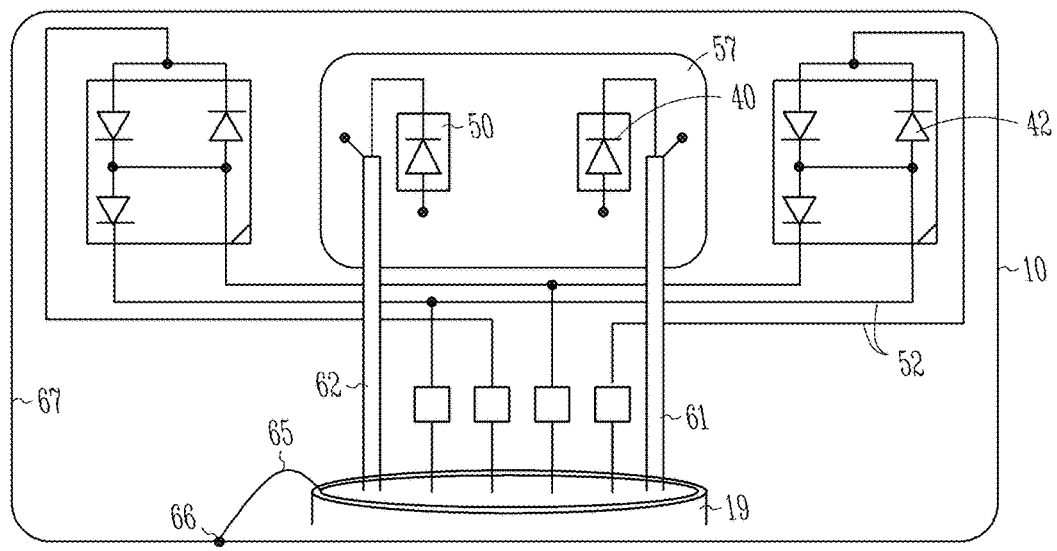
FIG. 4 is an electrical schematic of the sensor assembly of FIG. 2.

FIG. 4 illustrates an electrical schematic of an embodiment of sensor 10. Cable 19 includes a pair of coaxial lines 61, 62 and a series of control lines connected to traces 52 at locations 63A, 63B, 63C, and 63D shown in FIG. 3. The shields of coaxial lines 61, 62 connect to shield conductor 57. The center conductors of coaxial lines 61, 62 connect to cathode terminals T1 and are shielded by shield elements 55. The conductor bundle of cable 19 can be in the form of a shielded cable, i.e., having a metallic braid or mesh sleeve 65 which peripherally surrounds the electrical conductors (which are mutually insulated from one another). Mesh sleeve 65 is connected to a ring trace 66 at location 67. In one example, location 67 includes a shield component. The shield component can include a metal housing, a conductive housing, or other structure to limit undesirable effects of electromagnetic interference.

Figure 5:
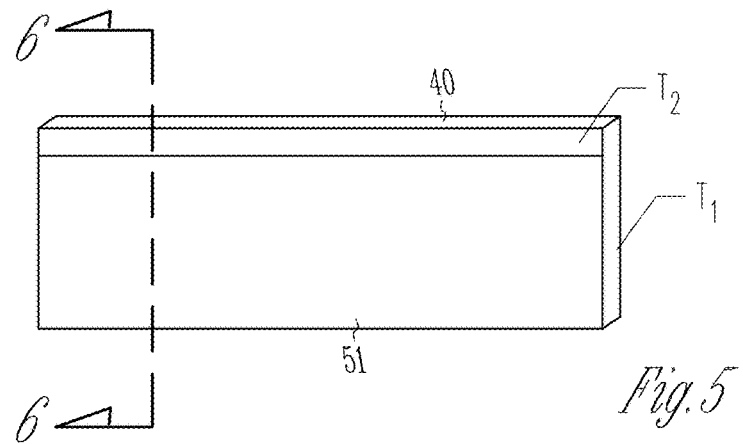
FIG. 5 is a perspective view of a planar photodetector.

FIG. 5 is a perspective illustration of photodetector 40. In one embodiment, photodetector 40 is a planar solderable photodiode. Photodetectors 40 includes an anode terminal, T2, and a cathode terminal, T1. In one example, an active (sensing) area 51 is defined on the same side as anode terminal, T2.

Figure 2:
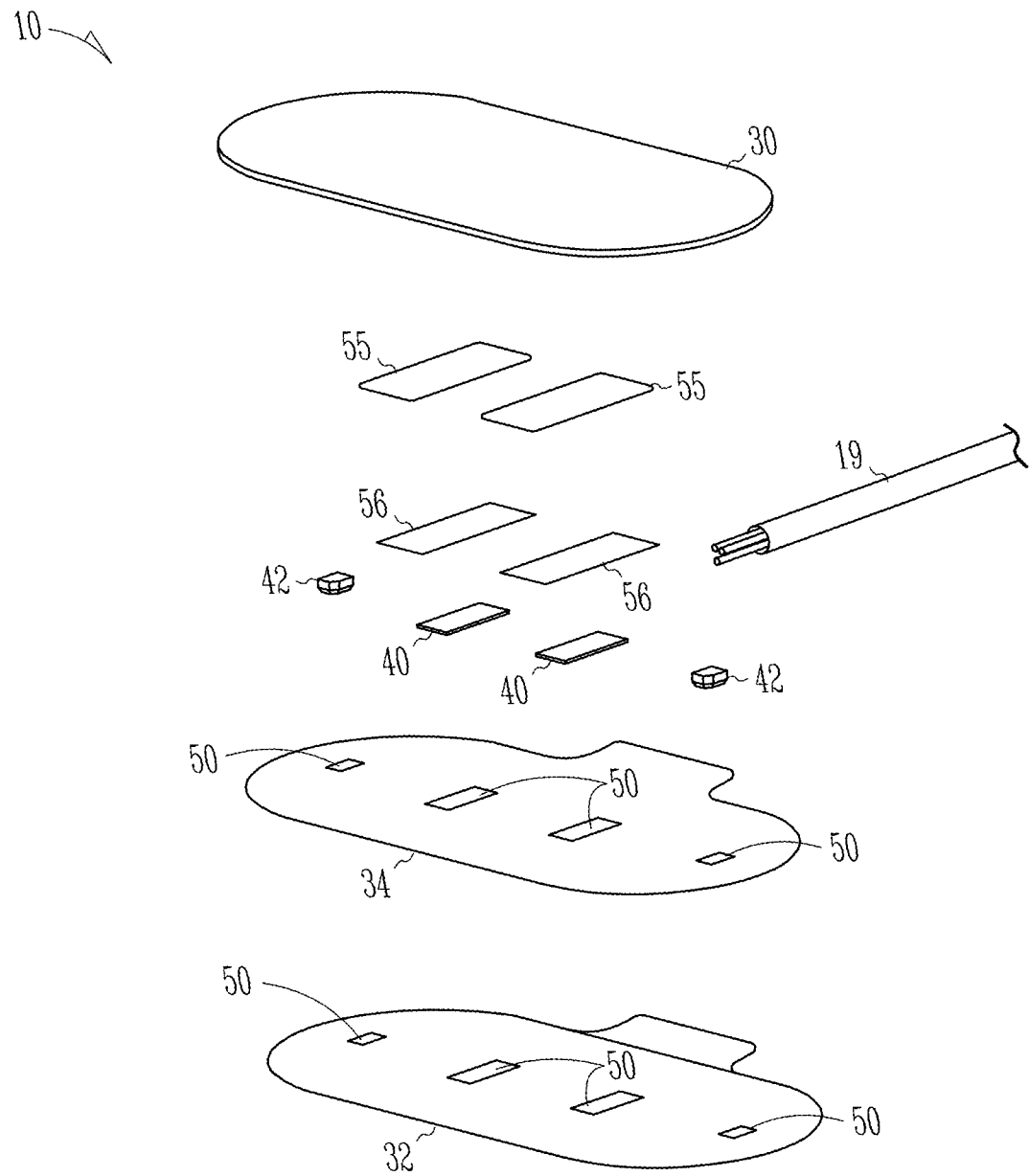
FIG. 2 is an exploded perspective view of a sensor assembly.
Figure 6:
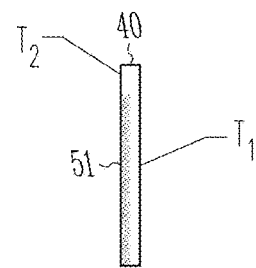
FIG. 6 is a cross sectional view of the photodetector of FIG. 5 taken along lines 6-6.
Figure 7:
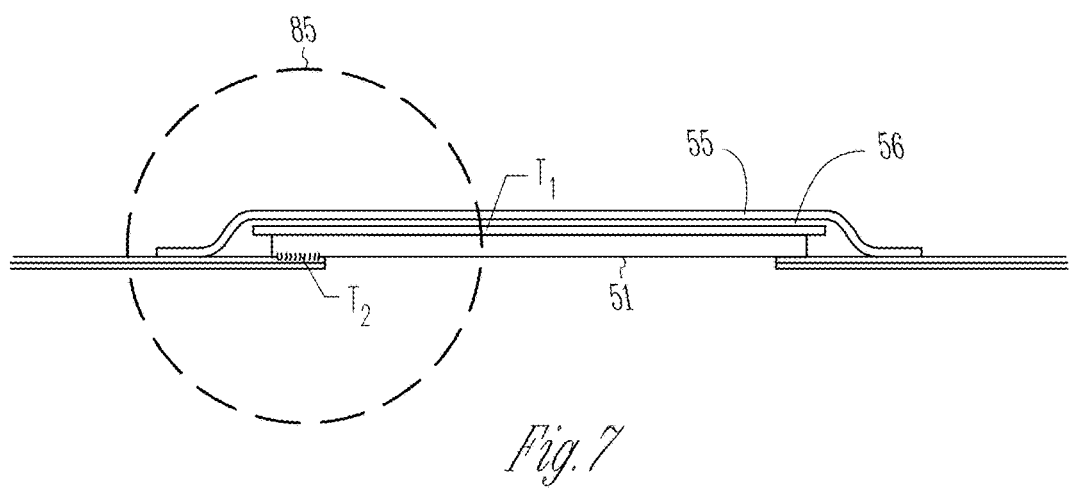
FIG. 7 is a cross sectional view of the sensor assembly of FIG. 2 taken through a photodetector 40.
Figure 8:
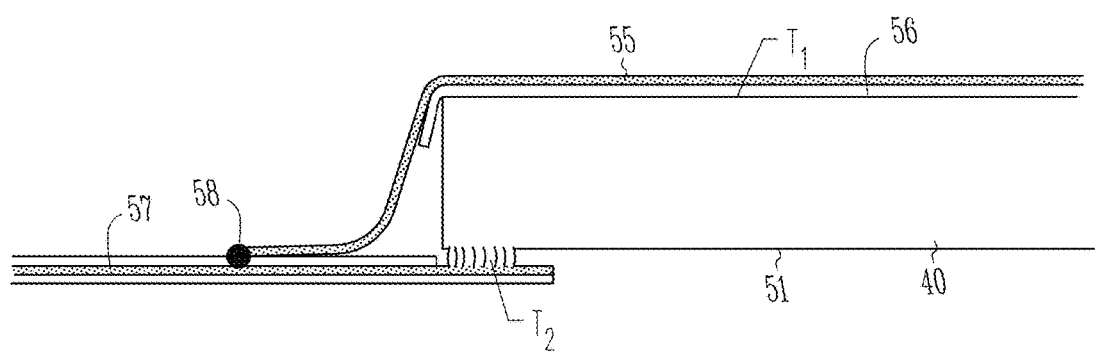
FIG. 8 is an enlarged portion of the view of FIG. 7.

FIG. 6 is a cross sectional view of the photodetector 40 of FIG. 5 taken along lines 6-6. FIG. 7 depicts a cross sectional view taken through sensor assembly 10. FIG. 8 illustrates detailed portion 85 (denoted by the dashed line circle) of FIG. 7. As shown, photodetector 40 is directly connected to shield 57 at terminal T2. The electrical connection can be via solder, conductive epoxies, or other techniques. As shown in FIGS. 2, 6 and 7, the photodetector 40 is larger in size than apertures 50 of circuit board 34. In one embodiment, apertures 50 are entirely covered by active areas 51 of the photodetectors 40. In one embodiment, photodetectors 40 are directly soldered to the shield conductor 57 at terminals T2 and the overlying shield elements 55 are also soldered to shield conductor 57 as shown in FIG. 3. In other embodiments, photodetectors 40 may be operatively coupled to the shield conductor 57 via techniques, such as conductive epoxies.

Figure 9:
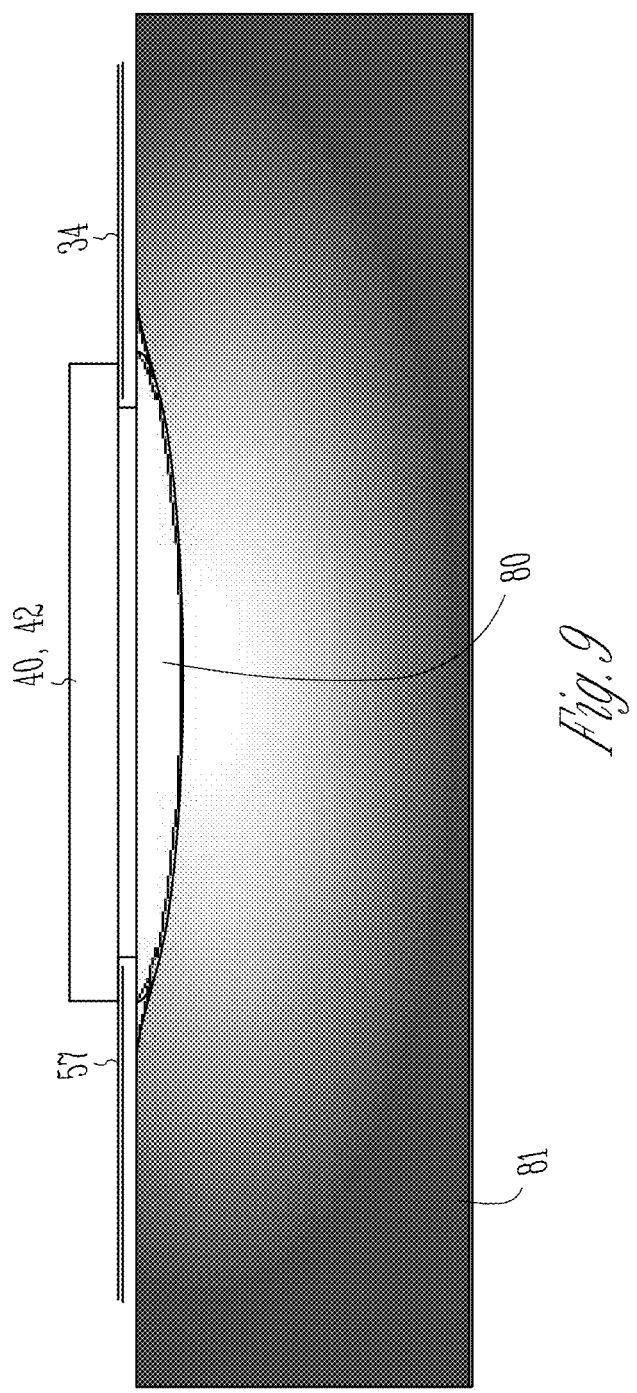
FIG. 9 depicts a blanching structure of an embodiment of the present subject matter as applied to a tissue site.

FIG. 9 depicts another cross sectional view of sensor assembly 10 wherein an optically transparent bump feature 80 extends from a lower surface of sensor 10 and is positioned between a light emitting device and/or light detector and tissue site 81. When sensor assembly 10 is applied at tissue site 81, bump feature 80 functions to blanch tissue immediately under the bump feature by applying an increased pressure to the tissue. The blood-blanched tissue reduces nearby light absorbance which in turn increases signal quality. Bump feature 80 further functions to increase the effective area for light to/from light emitting devices 42 and photodetectors 40 to enter and/or leave the tissue, further increasing signal quality. Bump feature 80 may also provide more consistent and reliable contact with the tissue surface. Bump feature 80 is formed by clear molded plastic or clear epoxy, encapsulant, or adhesive. Bump feature 80, in one example, protrudes sufficiently from a surface of sensor assembly 10 in order to blanch the tissue in the region of interest.

In one embodiment, light emitting devices 42 are light emitting diodes (LEDs). There may be several different individual such LEDs, each for producing a specifically selected different light wavelength. While it is also possible to implement the present subject matter in other configurations, e.g., with remotely located light-producing elements and fiberoptic conductors and emitters, the configuration illustrated provides certain advantages, particularly in conjunction with present-day LEDs, which can provide high light intensity from a very small component with relatively low excitation.

The relative separation (distance between) the light emitting devices 42 and the photodetectors 40 relates to the particular purpose, function and application of the system which the sensor assembly 10 is to be used. In one example, the relative separation (distance) effectively determine the location and size of the particular internal region which is to be selectably examined by the interrogating light wavelengths. In one embodiment, the distances between the emitters and detectors are substantially equivalent. Additional details regarding spacing of the light emitting devices 42 relative to photodetectors 40 may be found in the above-referenced application, U.S. Ser. No. 11/078,399. However, in the broader aspects of the underlying subject matter, various such distances may be determined and specified without otherwise changing the overall nature of the apparatus and methodology.

Figure 10:
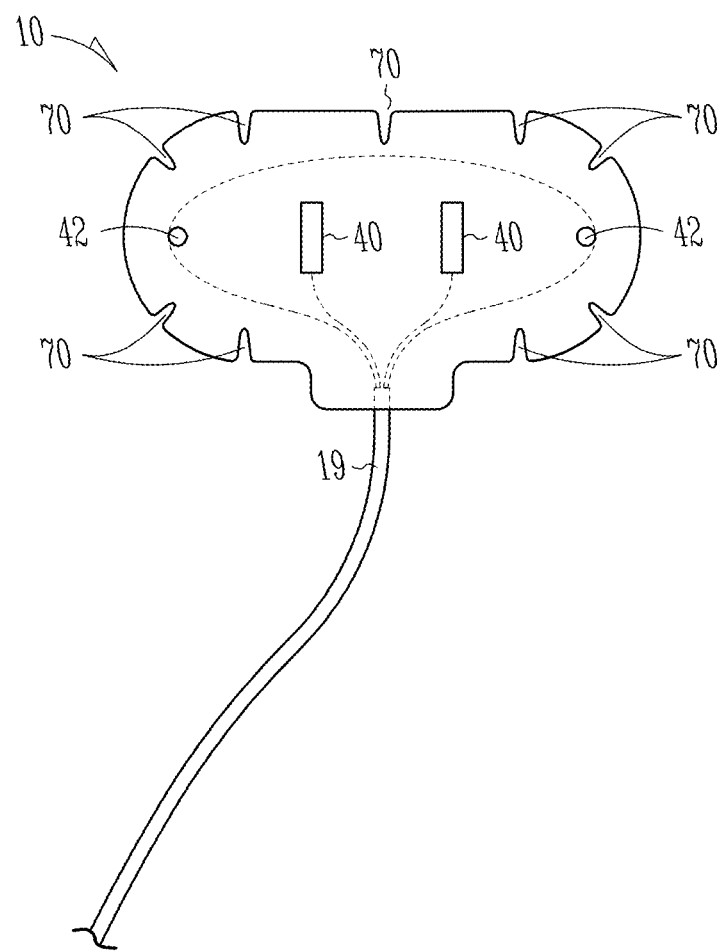
FIG. 10 is a top plan view of another embodiment of the present subject matter.

FIG. 10 illustrates another embodiment of the sensor assembly 10. Relief features 70 are provided around the perimeter of the sensor body to permit greater conformity to a smaller or "spherically" shaped surface, such as a forehead. The relief features 70 can be located away from the photodetectors 40 for improved immunity to ambient light. Relief features 70 may include slits, slots, cut-outs, etc.

Further general aspects of the sensor assembly 10 include the following. The frontal layer 32 may be of black, light-absorbing material, in order to more effectively isolate ambient light from the photodetectors, as well as to minimize the possibility of surface leakage between light emitting devices 42 and photodetectors 40. This helps ensure that photons received by the detectors have actually transmitted the tissue of the patient, and thus carry desired information. The cover layer 30 of the sensor assembly 10 can be opaque to ambient light, i.e., is of dense black material such as a sheet of polymeric foam material.

In the actual usage of the sensor assembly 10, it is applied to anatomical surfaces which are not likely to be perfectly flat, and which on the contrary are at least moderately curved; in fact, such curvature is likely to be compound in nature (i.e., not simply cylindrical), and the nature and extent of such curvature will vary from patient to patient, with a considerable degree of variation between some individuals.

An optical sensor assembly 10 of the present subject matter has a photodetector 40 which is directly connected to a shield conductor 57. In one example, the photodetector 40 is soldered directly to a shield conductor 57 proximate to an aperture 50 of the shield conductor. The photodetector's active area 51 can be larger in size than the shield conductor aperture 50. The shield conductor 57 may be defined as a conductive layer of a flexible circuit board 34. In another embodiment, the shield conductor 57 may be one side of an enclosed structure, such as a hollow conductive box. By mounting the active side 51 of photodetector 40 directly to the shield conductor 57, deleterious effects of capacitive coupling to the patient body or nearby objects can be reduced or eliminated.

In one embodiment, the sampling rate of system 8A or system 8B occurs at a subharmonic frequency of 50/60 hertz, such as 18.75 hertz. Sampling at such frequency provides improved digital filter performance and interference rejection.

In one embodiment, the sensor assembly 10 includes a memory in which information related to the sensor's use, manufacture or condition may be stored. For example, sensor assembly 10 may store sensor-specific spectral and/or calibration information accessible to a remote monitor or other control. Sensor assembly 10, pod 110, or both sensor assembly 10 and pod 110 can incorporate subject matter relating to on-sensor data storage disclosed in U.S. Ser. No. 11/039,760, entitled Sensor System with Memory and Method of Using Same, incorporated by reference herein for all purposes.

In another embodiment, the sensor body may be provided in a more monolithic form, and even as a one-piece integrally molded part, rather than in the illustrated layered constructions. Such a one-piece structure may simplify manufacturing, and may achieve other economies as well. In one example, the electro-optical components are sealed in place and not exposed to the environment, and may be embedded integrally (with their connective wiring, shielding, etc.) inside either an integrally molded or a permanently joined and completely sealed laminate body structure.

Additional Notes

One embodiment of a sensor assembly includes a light emitting device which emits light into a tissue field, a photodiode having a generally planar active area and receiving some of the emitted light, and a flexible conductive shield element conforming to a surface of said tissue field, with the photodiode covering an aperture of the shield element, and with an area of said aperture being smaller than the photodiode active area.

One embodiment of the sensor assembly 10 has a conductive shield element formed as a flex circuit. The sensor assembly 10 has a photodiode terminal adjacent to the active area, with the terminal being electrically connected to a conductor of the shield element. The photodiode may be a solderable photodiode. The conductive shield element is a flex circuit with a terminal of the photodiode directly soldered to the conductive shield element proximate to the aperture. The sensor assembly of the first embodiment includes a second terminal on a photodiode side opposite the active area. The second terminal in this embodiment is a cathode terminal of the photodiode. The sensor assembly 10 has a flexible conductive foil-like shield secured over the photodiode and being conductively connected to the shield element. The sensor assembly also includes an insulator for preventing electrical coupling between a cathode terminal of the photodiode and the conductive cover. The sensor assembly 10 has an adhesive layer for securing the sensor assembly to the tissue field.

Although the present subject matter and some advantages have been described in detail, it should be understood that various changes, substitutions and alterations can be made herein without departing from the spirit and scope of the invention. Moreover, the scope of the present application is not intended to be limited to the particular embodiments of the process, machine, manufacture, composition of matter, means, methods and steps described in the specification. As one of ordinary skill in the art will readily appreciate from the disclosure of the present subject matter, processes, machines, manufacture, compositions of matter, means, methods, or steps, presently existing or later to be developed that perform substantially the same function or achieve substantially the same result as the corresponding embodiments described herein may be utilized according to the present subject matter.

What is claimed is:

1. A system comprising:
    a monitor; and
    a sensor assembly coupled to the monitor by a cable, the sensor assembly including a circuit board electrically coupled to at least one light emitting device and coupled to at least one photodetector, the at least one light emitting device configured to emit light into a tissue and the at least one photodetector configured to provide an output signal on a cathode terminal of the at least one photodetector, the output signal based on light detected by a planar active area of the at least one photodetector, the planar active area aligned with an aperture in a conductor of the circuit board, the conductor electrically connected to an anode terminal on a side of the planar active area of the photodetector; and
    wherein the monitor is configured to receive data corresponding to the output signal and corresponding to at least one of oximetry information for the tissue and physiological information for the tissue.

2. The system of claim 1 wherein the sensor assembly includes a perimeter and a plurality of relief features distributed about the perimeter.

3. The system of claim 1 wherein the sensor assembly is configured to couple with a spherically shaped surface.

4. The system of claim 1 wherein the sensor assembly includes a bump feature on a surface, the bump feature configured to blanch a region of the tissue.

5. The system of claim 1 wherein the at least one light emitting device includes a fiber optic element.

6. The system of claim 1 wherein the at least one light emitting device includes a light emitting diode (LED).

7. The system of claim 1 wherein the circuit board includes a flexible circuit board.

8. The system claim 1 wherein the at least one photodetector is soldered to the conductor.

9. The system of claim 1 wherein the at least one photodetector is affixed to the circuit board by an adhesive.

10. The system of claim 1 wherein the monitor includes a visual display.

11. The system of claim 1 further including a pod coupled to the cable, the pod having a memory configured to store data corresponding to the sensor assembly.

12. The system of claim 11 wherein the pod includes a processor and wherein the memory is configured to store executable instructions for the processor.

13. The system of claim 11 wherein the pod includes a communication module configured to communicate with the monitor.

14. The system of claim 13 wherein the communication module is configured for wireless communication.

15. An apparatus comprising:
    a sensor body;
    a circuit board enclosed within the sensor body, the circuit board having at least one conductive trace and the conductive trace having at least one aperture;
    a cable coupled to the at least one conductive trace, the cable having a shield conductor and a signal conductor;
    at least one light emitting device coupled to the circuit board, the at least one light emitting device configured to emit light into a tissue;
    at least one photodetector having an anode terminal on a side of a planar active area coupled to the conductive trace, the at least one photodetector configured to provide an output signal on a cathode terminal of the at least one photodetector, the output signal based on light detected by the planar active area, the planar active area aligned with the aperture and the anode terminal electrically connected to the shield conductor; and
    wherein the cathode terminal is electrically connected to the signal conductor.

16. The apparatus of claim 15 wherein the sensor body includes a perimeter and a plurality of relief features distributed about the perimeter.

17. The apparatus of claim 15 wherein a surface of the sensor body includes foam.

18. The apparatus of claim 17 wherein the foam is black.

19. The apparatus of claim 15 wherein a surface of the sensor body includes an adhesive.

20. The apparatus of claim 15 wherein an end of the cable is configured to couple with a monitor.

21. The apparatus of claim 15 further including a conductive adhesive connection to the at least one conductive trace.

22. The apparatus of claim 15 further including a solder connection to the at least one conductive trace.

23. The apparatus of claim 15 wherein the circuit board includes a flexible circuit board.

24. The apparatus of claim 15 wherein the sensor body is configured to couple with a spherically shaped surface.

25. The apparatus of claim 15 wherein the sensor body includes a bump feature on a surface, the bump feature configured to blanch a region of the tissue.

26. The apparatus of claim 15 wherein the at least one light emitting device includes a fiber optic element.

27. The apparatus of claim 15 wherein the at least one light emitting device includes a light emitting diode (LED).

28. The apparatus of claim 15 wherein the at least one photodetector is soldered to the circuit board.

29. The apparatus of claim 15 wherein the at least one photodetector is affixed to the circuit board by an adhesive.

30. A method comprising:
    coupling at least one light emitting device to a circuit board;

coupling a photodetector to the circuit board, the photodetector having an anode terminal on a side of a planar active area, the planar active area aligned with an aperture of the circuit board and aligned with an aperture of a shield conductor of the circuit board, and the anode terminal electrically connected to the shield conductor of the circuit board, and the photodetector having a cathode terminal configured to provide an output signal based on light detected by the planar active area;

coupling a shield of a cable to the shield conductor of the circuit board and coupling a signal conductor of the cable to the cathode terminal; and assembling the circuit board to a sensor body, the sensor body having an adhesive surface.

31. The method of claim 30 further including forming at least one relief feature at a perimeter of the sensor body.

32. The method of claim 30 further including forming a bump feature on a surface of the sensor body, the bump feature configured to blanch a region of tissue when the sensor body is affixed to the tissue.

33. The method of claim 30 wherein coupling the at least one light emitting diode includes forming at least one of a conductive adhesive joint and a soldered joint.

34. The method of claim 30 wherein coupling the at least one photodetector includes forming at least one of a conductive adhesive joint and a soldered joint.

35. The system of claim 1 further comprising;

an insulator disposed on the at least one photodetector;

a conductive shield tape electrically connected to the conductor, the conductive shield tape configured to overlay the at least one photodetector and the insulator, and wherein the insulator is configured to electrically isolate the at least one photodetector from the conductive shield tape.

* * * * *